United States Patent
Butler et al.

(10) Patent No.: US 9,615,868 B2
(45) Date of Patent: Apr. 11, 2017

(54) BONE FASTENER AND METHODS OF USE

(71) Applicant: Warsaw Orthopedic, Inc., Memphis, TN (US)

(72) Inventors: Brian Butler, Atoka, TN (US); William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 197 days.

(21) Appl. No.: 14/271,159

(22) Filed: May 6, 2014

(65) Prior Publication Data

US 2015/0320465 A1 Nov. 12, 2015

(51) Int. Cl.
*A61B 17/86* (2006.01)
*A61B 17/70* (2006.01)

(52) U.S. Cl.
CPC ...... *A61B 17/8605* (2013.01); *A61B 17/7035* (2013.01); *A61B 17/7037* (2013.01); *Y10T 29/49828* (2015.01)

(58) Field of Classification Search
CPC ............ A61B 17/7032; A61B 17/7035; A61B 17/7037
See application file for complete search history.

(56) References Cited

U.S. PATENT DOCUMENTS

| | | | |
|---|---|---|---|
| 8,100,946 B2* | 1/2012 | Strausbaugh | A61B 17/7032 606/266 |
| 9,198,694 B2* | 12/2015 | Mishra | A61B 17/7082 |
| 2013/0150852 A1* | 6/2013 | Shluzas | A61B 17/7032 606/65 |

* cited by examiner

*Primary Examiner* — Andrew Yang

(57) ABSTRACT

A bone fastener includes a first portion that defines a longitudinal axis and includes an inner surface defining an implant cavity. An intermediate portion includes a first part having a wall including a first end surface that defines at least a portion of the implant cavity and a second end surface. The intermediate portion further includes a second part having a wall including an end surface connected with the second end surface of the first part and an inner surface. The second part is rotatable relative to the first part. A second portion includes a first end engageable with the inner surface of the second part and a second end configured to penetrate tissue. Systems and methods are disclosed.

20 Claims, 7 Drawing Sheets

BONE FASTENER AND METHODS OF USE

TECHNICAL FIELD

The present disclosure generally relates to medical devices for the treatment of spinal disorders, and more particularly to a surgical implant system including a bone fastener that provides stabilization while reducing stress on spinal elements.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, a bone fastener is provided. The bone fastener includes a first portion that defines a longitudinal axis and includes an inner surface defining an implant cavity. An intermediate portion includes a first part having a wall including a first end surface that defines at least a portion of the implant cavity and a second end surface.

The intermediate portion further includes a second part having a wall including an end surface connected with the second end surface of the first part and an inner surface. The second part is rotatable relative to the first part. A second portion includes a first end engageable with the inner surface of the second part and a second end configured to penetrate tissue. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
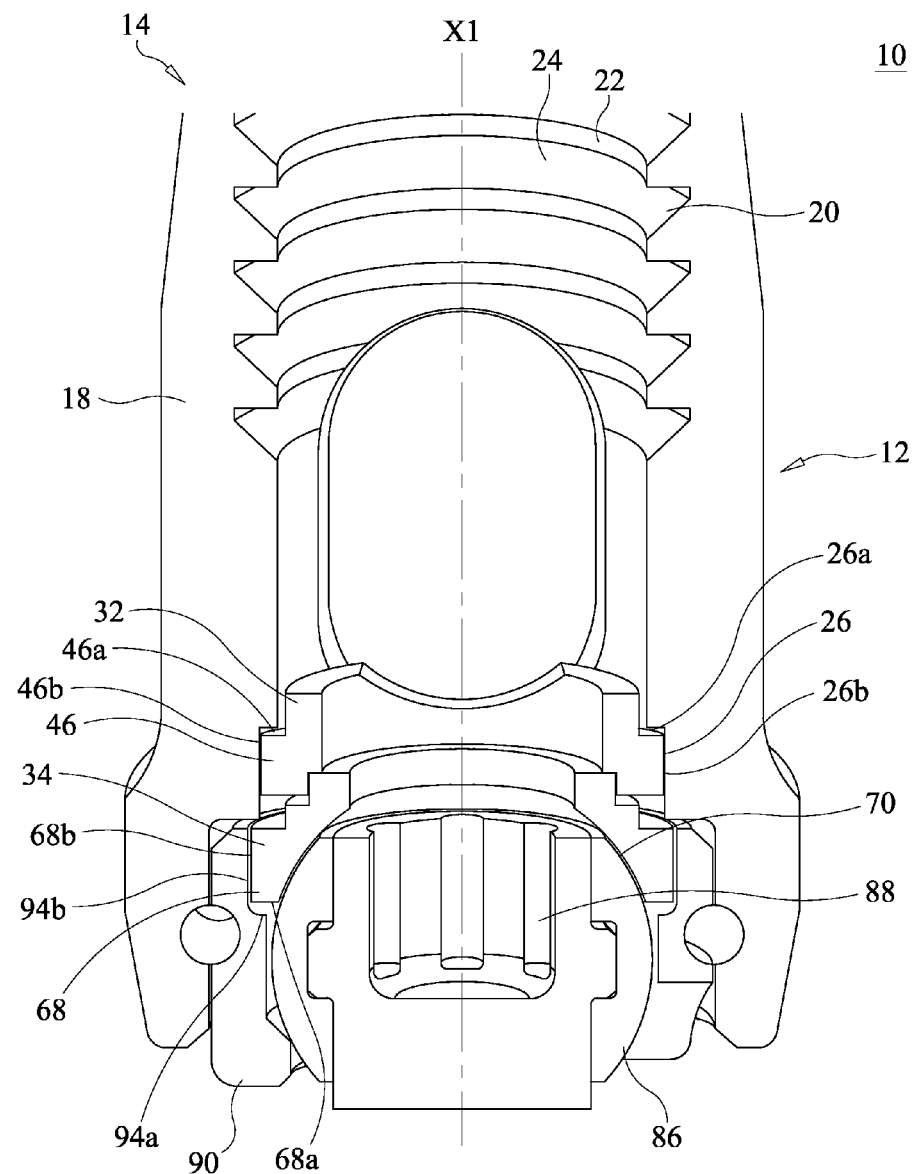
FIG. 1 is a break away cross section view of components of one embodiment of a spinal implant system in accordance with the principles of the present disclosure.
Figure 2:
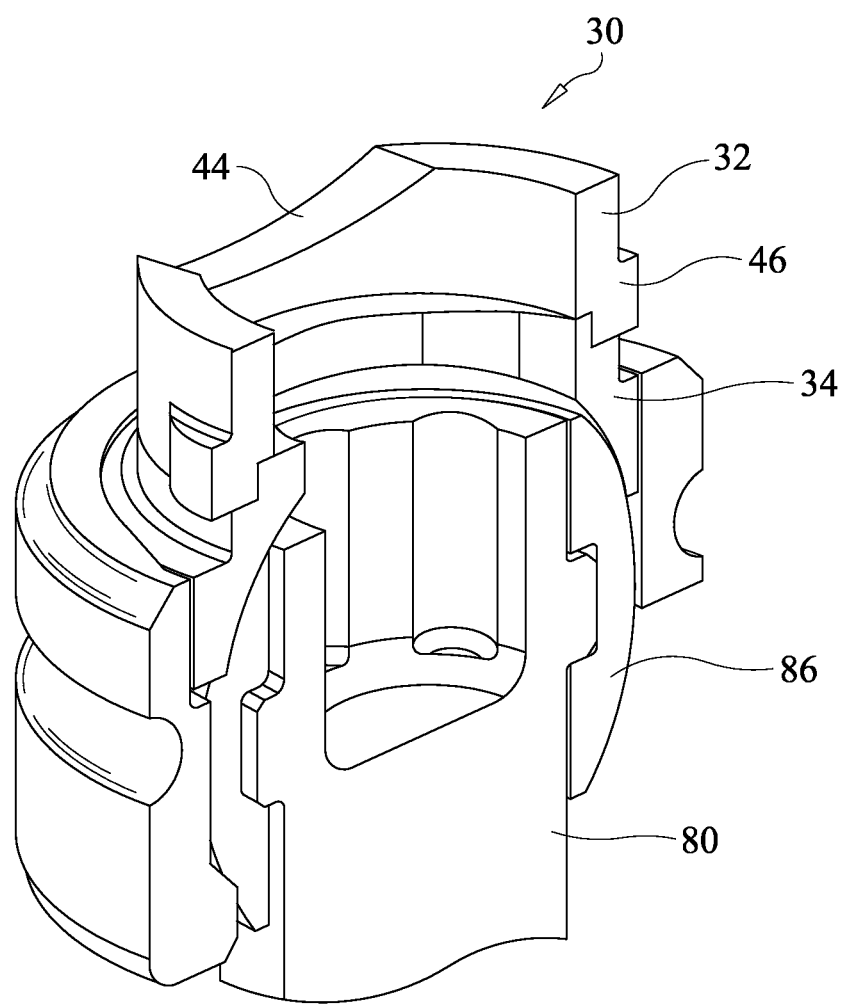
FIG. 2 is a cutaway view of the components shown in FIG. 1.
Figure 3:
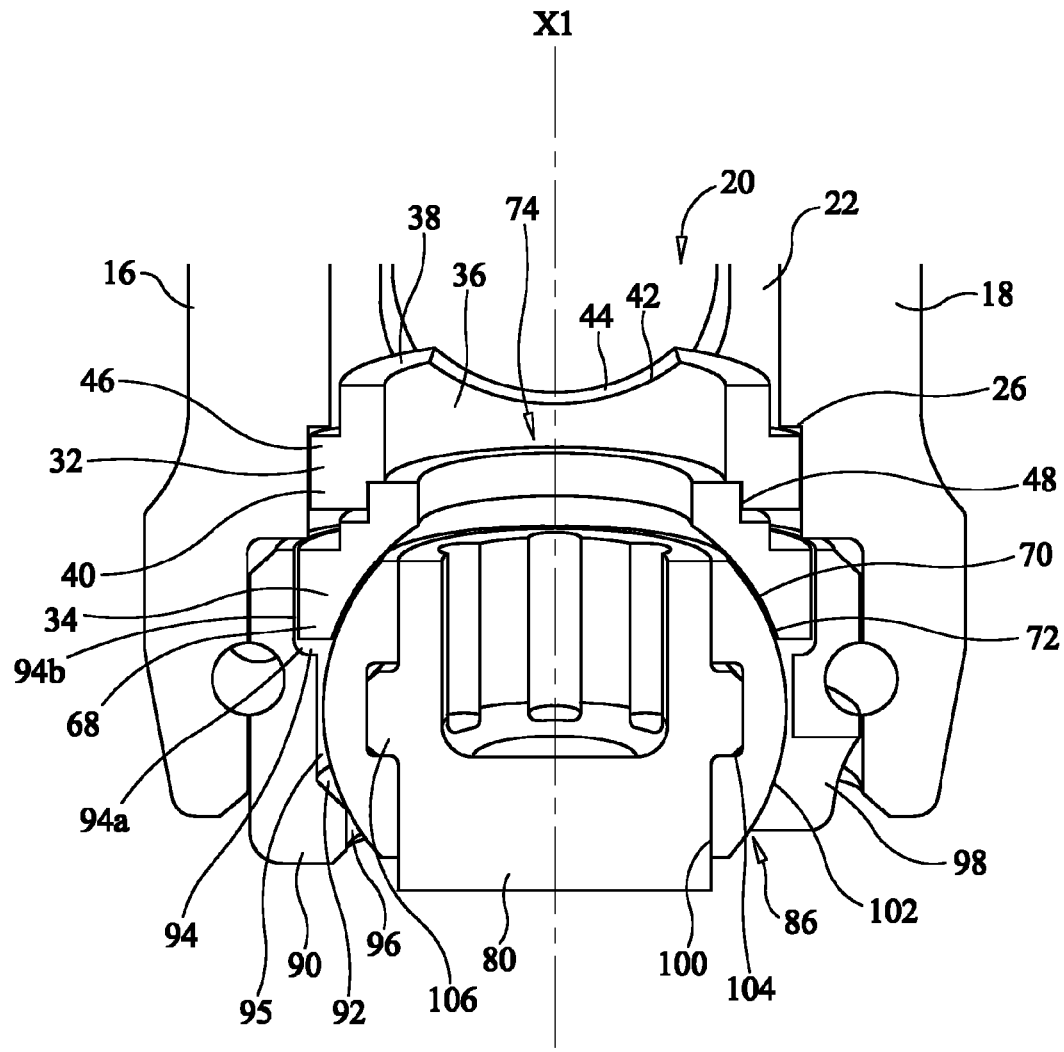
FIG. 3 is a break away view of the components shown in FIG. 1.
Figure 4:
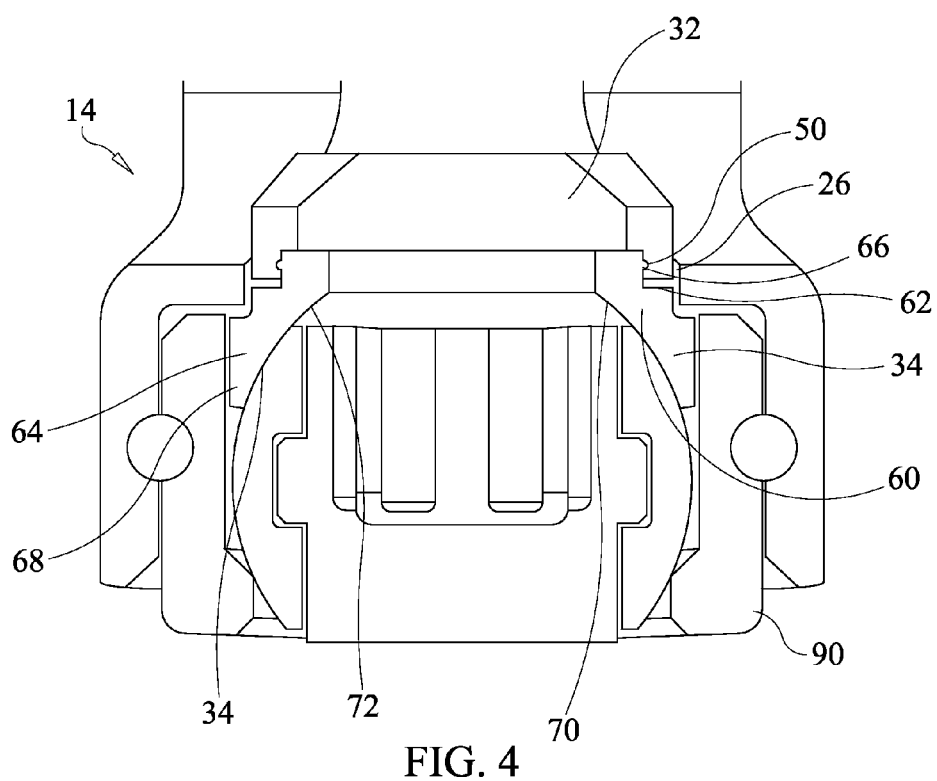
FIG. 4 is a break away view of the components shown in FIG. 1.

The exemplary embodiments of a surgical system and related methods of use disclosed are discussed in terms of medical devices for the treatment of musculoskeletal disorders and more particularly, in terms of a spinal implant system including a bone fastener. In some embodiments, the spinal implant system includes a bone fastener comprising a biased screw design. In some embodiments, the spinal implant system includes a bone fastener comprising a crown having a top part that seats a spinal rod and a bottom part that orients an opening in a base of a receiver of the bone fastener for disposal of a shaft.

In one embodiment, the system includes a bone fastener including a two piece crown. In one embodiment, the system includes a crown having a top piece, with a keyed fit into slots of a head of the bone fastener. In one embodiment, the system includes a two piece crown having a top piece configured for engagement with a counter bore of a head of the bone fastener. In one embodiment, the system includes a two piece crown having a top piece configured for engagement with a head of the bone fastener to prevent the top piece from rotating. In one embodiment, the system includes a two piece crown having a top piece configured for engagement with a head of the bone fastener to prevent the top piece from axial translation.

In one embodiment, the system includes a two piece crown having a top piece configured for engagement with a bottom piece, In one embodiment, the system includes a two piece crown having a groove and notch to lock a top piece with the bottom piece. In one embodiment, the system includes a two piece crown having a spring relief to facilitate a top piece snap fitting onto a bottom piece.

In one embodiment, the system includes a two piece crown having a top piece with an indexed surface such that a spinal rod mating geometry is oriented to a rod accepting region of a receiver. In one embodiment, the indexed surface comprises a radial groove configured to receive a spinal rod. In one embodiment, the radial groove is configured to improve axial grip of the spinal rod. In one embodiment, the system includes a two piece crown having a bottom piece indexed to a carrier component such that the bottom piece can be utilized to index a cutout of the carrier or index an increased angulation plane. In one embodiment, the system includes a two piece crown having a top half and a bottom half disposed in contacting relation. In one embodiment, the system includes a two piece crown having a top half and a bottom half disposed in a nested engagement. In one embodiment, the system includes a two piece crown having a top half and a bottom half that can snap together.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The spinal implant system of the present disdosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro-discectomy instruments used to remove portions bulging or hemiated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference will now be made in detail to the exemplary embodiments of the present disclosure, which are illustrated in the accompanying figures. Turning to FIGS. 1-7, there are illustrated components of a spinal implant system 10 including a bone fastener 12.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

System 10 includes an implant, such as, for example, bone fastener 12. Fastener 12 includes a portion, such as, for example, a receiver 14 having a closed proximal end and extending along an axis X1. Receiver 14 includes a pair of spaced apart arms 16, 18 that connect with the dosed proximal end and define an implant cavity 20 therebetween configured for disposal of at least a portion of a spinal construct, which includes, such as, for example, a spinal rod. Arms 16, 18 each extend parallel to axis X1, as shown in FIG. 1. In some embodiments, arm 16 and/or arm 18 may be disposed at alternate orientations, relative to axis X1, such as, for example, transverse, perpendicular and/or other angular orientations such as acute or obtuse, coaxial and/or may be offset or staggered. Arms 16, 18 each include an outer surface extending between a pair of side surfaces of receiver 14. At least one of the outer surfaces and the side surfaces of arms 16, 18 have at least one recess or cavity configured to receive an insertion tool, compression instrument and/or instruments for inserting and tensioning fastener 12. While the embodiment in this configuration shows a closed head, it is understood that an open head configuration may be used with the present invention.

Cavity 20 is substantially cylindrical. In some embodiments, all or only a portion of cavity 20 may have alternate cross section configurations, such as, for example, V-shaped, W-shaped, oval, oblong triangular, square, polygonal, irregular, uniform, non-uniform, offset, staggered, and/or tapered. Cavity 20 includes an inner surface 22. Surface 22 includes a thread form 24 configured for engagement with a coupling member, such as, for example, a setscrew (not shown), to retain a spinal rod within cavity 20. In some embodiments, the inner surface of receiver 14 may be disposed with the coupling member in alternate fixation configurations, such as, for example, friction fit, pressure fit, locking protrusion/recess, locking keyway and/or adhesive, Surface 22 includes a cavity, such as, for example, a slot 26 configured to receive a flange of a crown 30, as discussed herein. Slot 26 includes surfaces 26a, 26b. In some embodiments, slot 26 comprises a counter bore of surface 22. In some embodiments, all or only a portion of the inner surface of receiver 14 may have alternate surface configurations to enhance engagement with the spinal rod and/or the setscrew such as, for example, rough, arcuate, undulating, mesh, porous, semi-porous, dimpled and/or textured.

An intermediate portion, such as, for example, a crown 30 is configured for disposal within cavity 20. Crown 30 includes a part 32 and a part 34. Part 32 includes a wall 36 having an end surface 38 and an end surface 40. Surface 38 is configured to define at least, a portion 42 of cavity 20. Portion 42 is defined by an outer surface 44 that defines a curved portion of part 32 configured for engagement with a spinal rod. In some embodiments, all or only a portion of surface 44 may have alternate cross section configurations, such as, for example, oval, oblong triangular, square, polygonal, irregular, uniform, non-uniform, offset, staggered, and/or tapered.

Surface 38 defines a receiver engagement portion, such as, for example, a flange 46 configured for mating engagement with slot 26. Flange 46 includes surfaces 46a, 46b. Flange 46 engages the surface of slot 26 in a keyed connection such that surface 46a abuts surface 26a and surface 46b abuts surface 26b. Engagement of flange 46 and slot 26 is configured to prevent rotation and/or axial translation of part 32 relative to surface 22 of receiver 14. As such, surface 44 is disposed in fixed alignment with surface 22 for disposal of a spinal rod. Surface 40 defines an engagement portion 48 configured for engagement with part 34 such that surface 40 is in a nested configuration with a portion of part 34. In one embodiment, surface 40 includes a groove 50 configured to receive a notch 66 of part 34 to lock part 32 with part 34.

Figure 5:
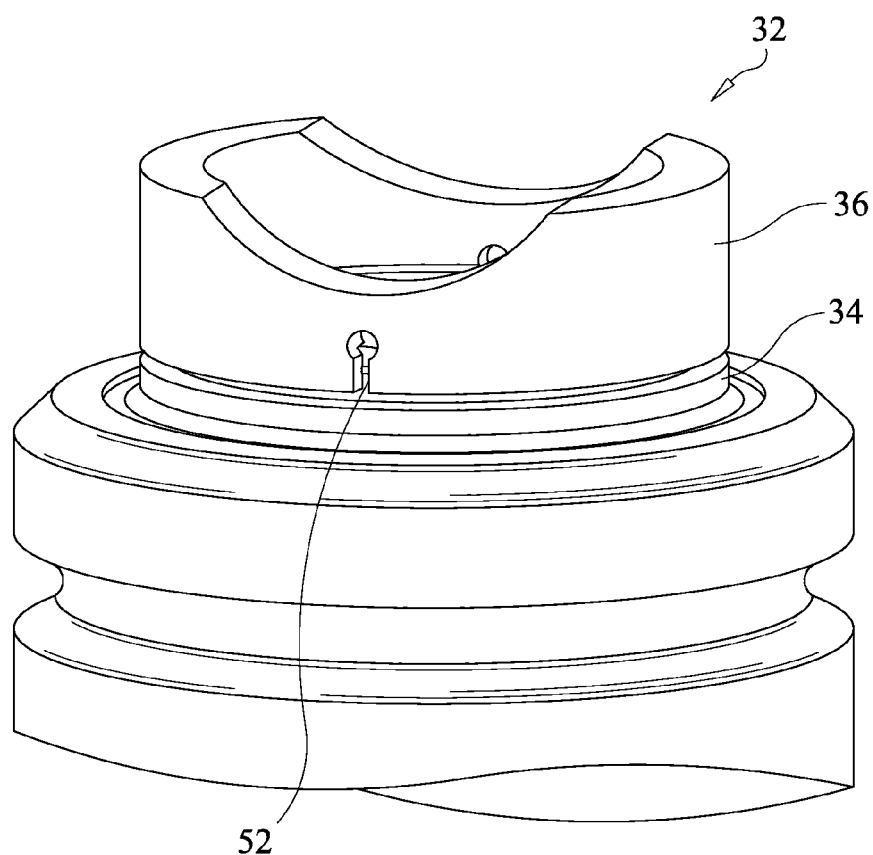
FIG. 5 is a cutaway view of the components shown in FIG. 1.

In one embodiment, as shown in FIG. 5, wall 36 includes at least one spring relief slot 52 configured to facilitate connection of part 32 with part 34. Slot 52 provides part 32 with flexibility so that groove 50 can flex and/or move about notch 66 for disposal of notch 66 within groove 50.

Part 34 includes a wall 60 having an end surface 62 and an end surface 64. Surface 62 is configured for engagement with surface 40. Surface 62 includes notch 66 configured for disposal with groove 50, as discussed herein. Surface 64 defines a carrier engagement portion, such as, for example, a flange 68. Flange 68 includes surfaces 68a, 68b configured for mating engagement with a slot 94 of a carrier 90, as discussed herein. Part 34 includes an inner surface 70. Surface 70 defines a curved portion 72 configured for engagement with a shaft 80, as discussed herein. In some embodiments, all or only a portion of surface 70 may have alternate cross section configurations, such as, for example, oval, oblong triangular, square, polygonal, irregular, uniform, non-uniform, offset, staggered, and/or tapered. Part 32 and part 34 define an opening 74 disposed in communication with cavity 20.

System 10 includes a carrier 90 disposed with receiver 14. Carrier 90 includes an inner surface 92 that defines a slot 94 and a cavity 95. Slot 94 includes surfaces 94a, 94b. The surfaces of slot 94 engage flange 68 in a keyed connection such that surface 68a abuts surface 94a and surface 68b abuts surface 94b.

Cavity 95 is configured for disposal of a retainer ring 86, as described herein. Surface 92 defines a flange 96 configured for engagement with ring 86 and retention of ring 86 with cavity 95. Ring 86 rotates within cavity 95 and shaft 80 is guided within cavity 95 to dispose shaft 80 into position for alignment and pivoting into an opening 98, as described herein. Surface 92 defines an arcuate lateral opening 98 configured for disposal of shaft 80 such that shaft 80 can be positioned with opening 98 for attaching implanted shaft 80 relative to a spinal rod disposed with receiver 14, as described herein.

Figure 6:
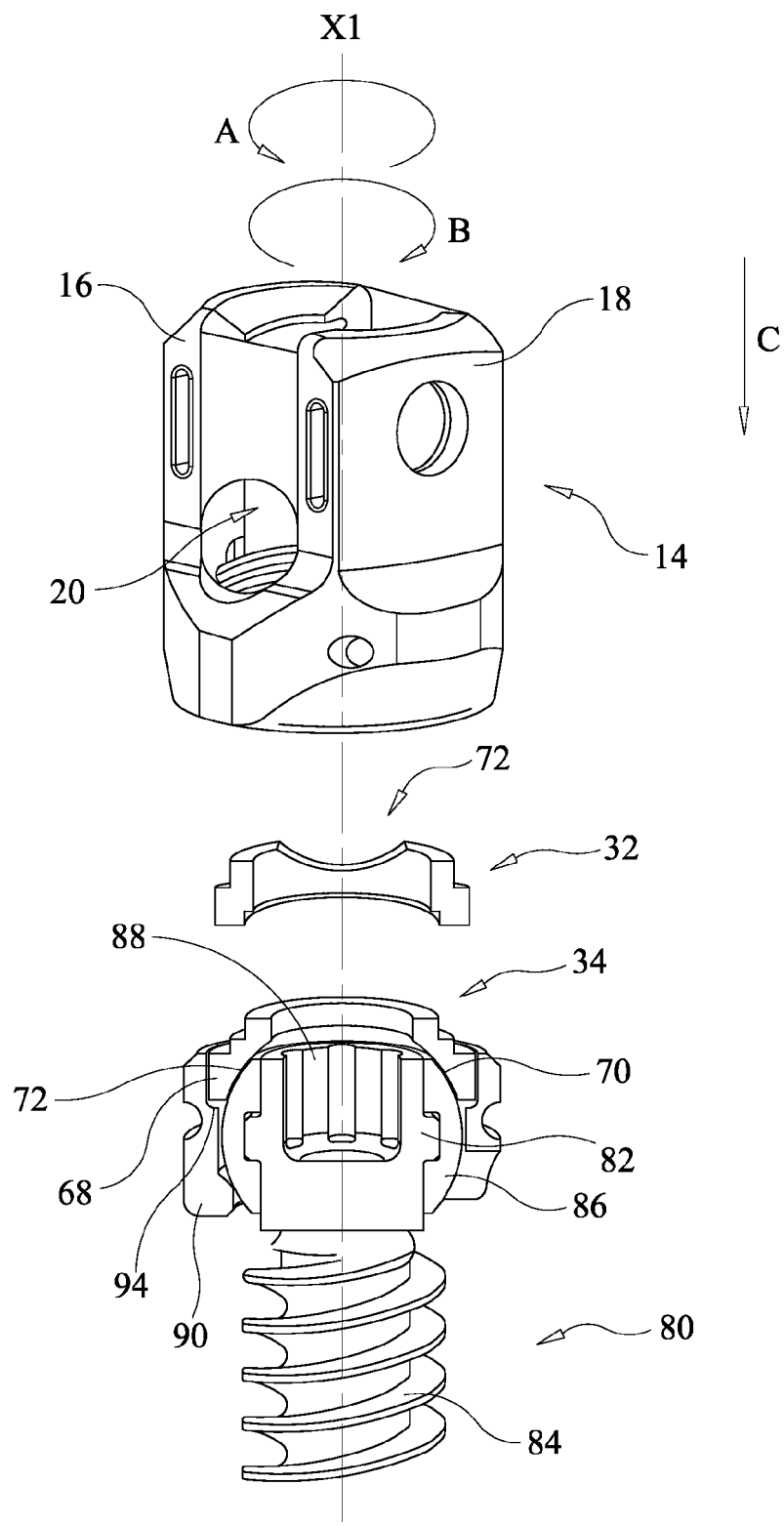
FIG. 6 is a perspective view of the components shown in FIG. 1 with parts separated.

Shaft 80 includes an end 82 disposed with surface 86 and a threaded end 84, as shown in FIG. 6, configured to penetrate tissue, such as, for example, bone. Ring 86 is mounted with end 82. Ring 86 includes an inner surface 100 and an outer surface 102. Inner surface 100 defines a groove 104 configured for disposal of a circumferential flange 106 disposed at end 82. In some embodiments, end 82 rotates relative to ring 86. In some embodiments, end 82 is fixed with ring 86. Surface 102 is configured for engagement with surface 92 of carrier 90. A flange 96 of carrier 90 is configured to receive ring 86 in a cavity 95 of carrier 90, as described herein. Ring 86 is substantially spherical in shape and is configured for engagement with curved portion 70. This configuration allows end 84 to be rotatable relative to axis X1, for example, for disposal with opening 98. Receiver 14 is rotatable relative to shaft 80 about axis X1 in a range of 0-180 degrees. In one embodiment, receiver 14 is rotatable relative to shaft 80 to a selected angle about axis X1.

Figure 7:
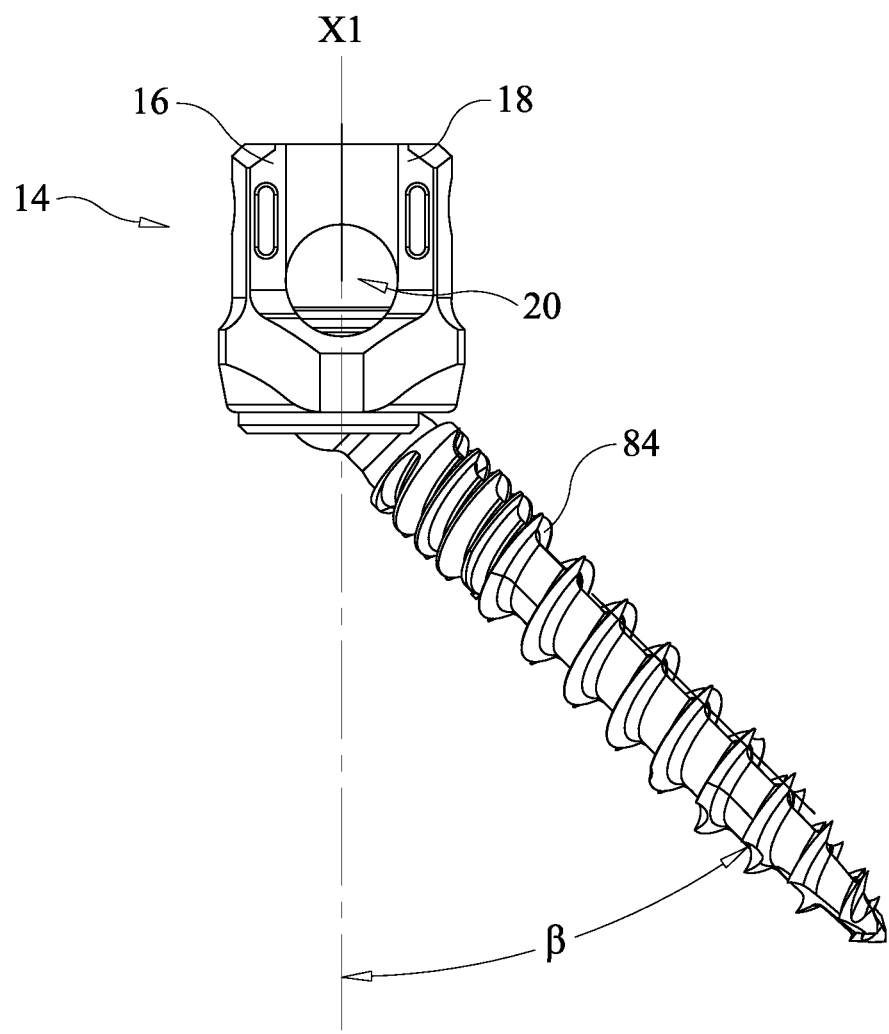
FIG. 7 is a side view of the components shown in FIG. 1.

End 84 is movable relative to receiver 14 between a first orientation in which shaft 80 is coaxial with axis X1, as shown in FIG. 6, and a second orientation in which end 84 is through an angular range, for example, an angular range β, of greater than 0 degrees through about 45 degrees relative to axis X1, as shown in FIG. 7. In some embodiments, opening 98 facilitates rotation of shaft 80 such that shaft 80 is disposed within opening 98 in the second orientation to for example, a maximum angle β relative to axis X1. In one embodiment, end 84 is rotatable to a selected angle through and within angular range β relative to axis X1. In some embodiments, end 84 is rotatable in a plurality of planes that lie in a cone configuration about receiver 14 that defines a range of motion of end 84 about axis X1. In one embodiment, end 84 is rotatable to a selected angle within angular range β in a sagittal plane of a body of a patient. In one embodiment, end 84 is rotatable to a selected angle within angular range β in a transverse plane of the body. In one embodiment, end 84 is rotatable to a selected angle within angular range β in a coronal plane of the body.

End 82 includes a socket 88 having a hexalobe geometry configured for disposal of a similarly shaped bit of a tool, such as, for example, a driver. The driver engages the surfaces of socket 88 to rotate shaft 80, in the direction shown by arrow A in FIG. 6, or, in the arrow B. Socket 88 is in communication with opening 74 and cavity 20 such that a driver may be inserted between arms 16, 18 and translated axially, in the direction shown by arrow C, until the bit of the driver is disposed in socket 88. In some embodiments, socket 88 has a cruciform, phillips, square, hexagonal, polygonal, star or hexalobe cross sectional configuration for disposal of a correspondingly shaped portion of a driver.

In assembly, operation and use, spinal implant system 10, similar to the systems and methods described herein, includes fastener 12 and is employed with a surgical procedure for treatment of a spinal disorder affecting a section of a spine of a patient, as discussed herein. Spinal implant system 10 is employed with a surgical procedure for treatment of a condition or injury of an affected section of the spine.

In use, to treat the affected section of the spine, a medical practitioner obtains access to a surgical site in any appropriate manner, such as through incision and retraction of tissues. In some embodiments, the components of spinal implant system 10 may be used in any existing surgical method or technique including open surgery, mini-open surgery, minimally invasive surgery including percutaneous surgical implantation. Once access to the surgical site(s) is obtained, the particular surgical procedure is performed for treating the spinal disorder. The components of spinal implant system 10 including fasteners 12 are employed to augment the surgical treatment. Fasteners 12 and one or a plurality of spinal implants, such as, for example, vertebral rods can be delivered or implanted as a pre-assembled device or can be assembled in situ. Spinal implant system 10 may be may be completely or partially revised, removed or replaced.

In one embodiment, the components of fastener 12 are assembled prior to implantation. In one embodiment, the components of fastener 12 are assembled in situ. Part 34 is translated, in the direction shown by arrow C in FIG. 6, along axis X1 onto shaft 80 such that portion 86 is disposed with surface 72 and flange 68 engages slot 94. Flange 68 engages slot 94 in a keyed connection such that surface 68a abuts surface 94a and surface 68b abuts surface 94b, as described herein.

Part 32 is translated, in the direction shown by arrow C, along axis X1 over part 34. Translation of part 32 over part 34 causes relief slot 52 to expand to facilitate a snap fit engagement of part 32 with part 34, as described herein. Notch 66 snaps into groove 50 to lock part 34 with part 32.

Surface 40 is disposed in a nested configuration with surface 62 of part 34. Flange 46 of part 32 is engaged with slot 26. Surfaces 26a, 46a engage surfaces 26b, 46b in a keyed connection to facilitate alignment and maintain a relative fixed orientation of the spinal rod. Engagement of flange 46 and slot 26 prevents rotation and/or axial translation of part 32 relative to receiver 14. Flange 96 engages ring 86 to guide shaft 80 into position for pivoting into opening 98. Opening 98 facilitates rotation of shaft 80 relative to receiver 14 and axis X1 through a maximum range of angle β.

Surface 44 is positioned within cavity 20 to receive the spinal rod. Opening 74 is aligned over socket 88 for disposal of a bit of a tool, such as, for example, a driver to engage the driver with shaft 80 to rotate shaft 80, as described herein. Socket 88 is in communication with opening 74 and cavity 20 such that a driver may be inserted between arms 16, 18 and translated axially, in the direction shown by arrow C, until the bit of the driver is disposed in socket 88. The driver is rotated causing fastener 12 to translate axially within a pilot hole, in the direction shown by arrow C in FIG. 6. Shaft 80 is threaded and engaged with tissue. In some embodiments, fastener 12 is disposed adjacent vertebrae at a surgical site and is manipulated to drive, torque, insert or otherwise connect fastener 12 with the vertebrae.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, system 10 may include one or a plurality of rods, plates, connectors and/or bone fasteners for use with a single vertebral level or a plurality of vertebral levels.

In some embodiments, one or more of fasteners 12 may be engaged with tissue in various orientations, such as, for example, series, parallel, offset, staggered and/or alternate vertebral levels. In some embodiments, one or more of fasteners 12 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
  a first portion defining a longitudinal axis and including an inner surface defining an implant cavity;
  an intermediate portion including a first part having a wall including a first end surface that defines at least a portion of the implant cavity and a second end surface, the intermediate portion further including a second part having a wall including an end surface connected with the second end surface of the first part and an inner surface, the second part being rotatable relative to the first part, the end surface of the second part including a notch and the second end surface of the first part including a groove configured to receive the notch; and a second portion including a first end engageable with the inner surface of the second part, a second end configured to penetrate tissue and a carrier that engages the inner surface of the first portion.

2. A bone fastener as recited in claim 1, wherein the first portion includes an inner surface defining a key connection engageable with the first part to prevent rotation of the first part.

3. A bone fastener as recited in claim 1, wherein the first portion includes an inner surface defining a key connection engageable with the first part to prevent axial translation of the first part.

4. A bone fastener as recited in claim 1, wherein the inner surface of the first portion defines a slot configured to receive a flange of the first part.

5. A bone fastener as recited in claim 1 wherein the inner surface of the first portion includes a counter bore configured to receive the first part.

6. A bone fastener as recited in claim 1, wherein the first portion is an implant receiver.

7. A bone fastener as recited in claim 1, wherein the first part includes an outer surface that defines a curved portion configured for engagement with an implant.

8. A bone fastener as recited in claim 1, wherein the carrier comprises a slot configured to receive a flange of the second part.

9. A bone fastener as recited in claim 1, wherein the second portion is a threaded shaft.

10. A bone fastener as recited in claim 1, wherein the first end of the second portion includes a third portion configured for disposal with the inner surface of the second part to facilitate rotation.

11. A bone fastener as recited in claim 10, wherein the third portion is spherical.

12. A bone fastener as recited in claim 10, wherein an inner surface of the carrier engages an outer surface of the third portion.

13. A bone fastener as recited in claim 1, wherein the notch snaps into the groove to lock the second part with the first part.

14. A bone fastener as recited in claim 1, wherein an outer surface of the carrier engages the inner surface of the first portion and an inner surface of the carrier engages an outer surface of the first part.

15. A bone fastener as recited in claim 1, wherein an outer surface of the carrier and the inner surface of the first portion each include a channel, a retainer being positioned within the channels to couple the carrier to the first portion.

16. A bone fastener comprising:
a receiver defining a longitudinal axis and including an inner surface defining an implant cavity;
a crown including a first part having a wall including a first end surface that defines at least a portion of the implant cavity and a second end surface,
the crown further including a second part having a wall including an end surface connected with the second end surface of the first part and an inner surface, the second part being rotatable relative to the first part, the end surface of the second part including a notch and the second end surface of the first part including a groove configured to receive the notch; and
a threaded shaft including a first end engageable with the inner surface of the second part, a second end configured to penetrate tissue and a carrier that engages the inner surface of the receiver,
wherein the inner surface of the receiver defines a key connection engageable with the first part to prevent axial translation of the first part and the inner surface of the receiver defines a slot configured to receive a flange of the first part, and the second end of the threaded shaft is movable relative to the receiver between a first orientation in which the threaded shaft is coaxial with the axis and a second orientation in which the threaded shaft is disposed in an angular orientation relative to the axis.

17. A bone fastener as recited in claim 16, wherein the first end of the threaded shaft includes a spherical fitting configured for disposal with the inner surface of the second part to facilitate rotation.

18. A bone fastener as recited in claim 16, wherein the notch snaps into the groove to lock the second part with the first part.

19. A bone fastener as recited in claim 16, wherein an outer surface of the carrier engages the inner surface of the receiver and an inner surface of the carrier engages an outer surface of the first part.

20. A method of assembly for a bone fastener, the method comprising the steps of:
providing a first portion defining a longitudinal axis and including an inner surface defining an implant cavity;
providing an intermediate portion including a first part having a wall including a first end surface that defines at least a portion of the implant cavity and a second end surface, the intermediate portion further including a second part having a wall including an end surface connected with the second end surface of the first part and an inner surface, the second part being rotatable relative to the first part, the end surface of the second part including a notch and the second end surface of the first part including a groove;
aligning the second end surface of the first part with the end surface of the second part and snapping the notch into the groove to fix the first part with the second part;
providing a second portion including a first end engageable with the inner surface of the second part a second end configured to penetrate tissue;
providing a third portion configured for disposal with the inner surface of the second part to facilitate rotation;
disposing the third portion on the first end of the second portion; and
engaging the first part with the second part to translate the second portion axially relative to the first portion.

* * * * *